(12) United States Patent
Badylak

(10) Patent No.: US 6,793,939 B2
(45) Date of Patent: Sep. 21, 2004

(54) BIOMATERIAL DERIVED FROM VERTEBRATE LIVER TISSUE

(75) Inventor: Stephen F. Badylak, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 113 days.

(21) Appl. No.: 10/134,416

(22) Filed: Apr. 29, 2002

(65) Prior Publication Data

US 2002/0160052 A1 Oct. 31, 2002

Related U.S. Application Data

(63) Continuation of application No. 09/319,781, filed as application No. PCT/US97/22727 on Dec. 10, 1997, now Pat. No. 6,379,710.
(60) Provisional application No. 60/032,680, filed on Dec. 10, 1996.

(51) Int. Cl.$^7$ ............................................. A61K 35/407
(52) U.S. Cl. ..................................................... 424/553
(58) Field of Search .......................................... 424/553

(56) References Cited

U.S. PATENT DOCUMENTS

| | | | |
|---|---|---|---|
| 4,352,887 A | 10/1982 | Reid et al. | |
| 4,642,292 A | 2/1987 | Reid et al. | |
| 4,645,669 A | 2/1987 | Reid | |
| 4,801,299 A | 1/1989 | Brendel et al. | 623/1.47 |
| 4,829,000 A | 5/1989 | Kleinman et al. | 435/408 |
| 4,902,508 A | 2/1990 | Badylak et al. | 424/423 |
| 5,275,826 A | 1/1994 | Badylak et al. | 424/551 |
| 5,281,422 A | 1/1994 | Badylak et al. | 623/13.11 |
| 5,352,463 A | 10/1994 | Badylak et al. | 424/551 |
| 6,379,710 B1 * | 4/2002 | Badylak | 424/553 |

FOREIGN PATENT DOCUMENTS

EP 218065 4/1987

OTHER PUBLICATIONS

Kleinman et al., *Formation of a Supramolecular Complex is Involved in the Reconstitution of Basement Membrane Components*, Biochemistry, vol. 22, 1983, pp. 4969–4974.

Kleinman et al., *Basement Membrane Complexes With Biological Activity*, Biochemistry, vol. 25, No. 2, Jan. 28, pp. 312–318.

Wewer et al., *Human Laminin Isolated in a Nearly Intact, Biologically Active Form From Placenta by Limited Proteolysis*, J. of Biol. Chem., vol. 258, No. 20, Oct. 25, 1983, pp. 12654–12660.

Madison et al., *Increased Rate of Peripheral Nerve Regeneration Using Bioresorbable Nerve Guides and a Laminin–Containing Gel*, Exp. Neurology, vol. 88, 1985, pp. 767–772.

Kleinman et al., *Isolation and Characterization of type IV procollagen, laminin, and heparan sulfate proteoglycan from the EHS sarcoma*, Biochemistry, vol. 21, 1982, pp. 6186–6193.

Vuklcevic et al., *Identification of Multiple Active Growth Factors In Basment Membrane Matrigel Suggests Caution In Interpretation Of Cellular Activity Related To Extracellular Matrix Components*, Exp. Cell. Res., vol. 202, pp. 1–8.

Saad et al., *Crude Liver Membrane Fractions And Extracellular Matrix Components As Substrata Regulate Differentially The Preservation And Inducibility Of Cytochrome Patent–450 Isoenzymes In Cultured Rat Hepatocytes*, Eur. J. Biochem., vol. 213, 1993, pp. 805–814.

Saad et al., *Crude Liver Membrane Fractions As Substrate Preserve Liver–specific Functions In Long–term Serum–free Rat Hepatocyte Cultures*, In Vitro Cell Dev. Bio., 29A;3240, Jan. 1993.

Rakotoarivony et al., Comptes Rendus Hebdomadaires Des Seances De L'Academie Des Sciences D: Sciences Natruelles 284(7):565–568 (Feb. 14, 1977). Abstract.

Carlson et al. Renal Physiology 3 (1–6): 280–287 (1980). Abstract.

Meezan et al., Biol. Chem. Basement Membr., [Proc. Int. Symp.] 1st (1978), Meeting Date 1976, 17–30. Abstract.

Dixit et al., Artif. Organs 16(4): 336–341 (1992). Abstract.

Gibbons et al., Eur. J. Biochem. 66(2): 243–250 (1976). Abstract.

\* cited by examiner

Primary Examiner—Jean C. Witz
(74) Attorney, Agent, or Firm—Barnes & Thornburg

(57) ABSTRACT

A tissue graft composition comprising liver basement membrane is described. The graft composition can be implanted to replace or induce the repair of damaged or diseased tissues.

14 Claims, No Drawings

BIOMATERIAL DERIVED FROM VERTEBRATE LIVER TISSUE

CROSS REFERENCE TO RELATED APPLICATIONS

This application is a continuation application of U.S. patent application Ser. No. 09/319,781, filed on Jun. 10, 1999, now U.S. Pat. No. 6,379,710, which is a U.S. national phase counterpart of international application serial No. PCT/US97/22727, filed Dec. 10, 1997, which claims priority to U.S. Provisional Application serial No. 60/032,680, filed on Dec. 10, 1996.

This invention was made with U.S. Government support under Grant #HD-31425 awarded by the National Institute of Health. The U.S. Government has certain rights in the invention.

FIELD OF THE INVENTION

The present invention relates to a tissue graft composition and methods for its preparation and use. More particularly, the present invention is directed to non-immunogenic tissue graft compositions comprising the basement membrane of liver and the use of same to promote endogenous tissue growth in vivo and to support the growth and differentiation of eukaryotic cells cultured in vitro.

BACKGROUND AND SUMMARY OF THE INVENTION

There has been much research effort directed to finding natural and synthetic materials having the requisite properties for use as tissue grafts. Surprisingly, it has been found that basement membranes (stroma) prepared from liver tissue of warm-blooded vertebrates by removing cellular components of the liver tissue exhibit certain mechanical and biotropic properties similar to that which has been reported for intestinal submucosal tissue in U.S. Pat. Nos. 4,902,508; 5,281,422; and 5,275,826. It can be substituted for intestinal submucosa tissue in most, if not all, of the applications previously reported for intestinal submucosa, including enhancing wound healing, promoting endogenous tissue growth, stimulating cell proliferation and inducing cell differentiation.

The basement membrane of the liver is an extracellular matrix distinct from submucosal extracellular matrices. The liver basement membrane does not support an overlaying mucosa and is devoid of the laminate tissue structure in which submucosal extracellular matrices reside. The liver plays a central role in numerous regulatory processes in the body, including glucose metabolism, insulin regulation, anabolic processes for the musco-skeletal system and central nervous system, and the maintenance of appropriate levels of circulating proteins essential for day to day homeostasis.

In one embodiment of the present invention, liver basement membranes are used to manufacture a non-immunogenic tissue graft composition for use in the repair of damaged or diseased tissues. The tissue graft composition of the present invention comprises the basement membrane of organ tissue of a warm-blooded vertebrate, for example, liver tissue, substantially free, preferably devoid, of all cells (e.g., hepatocytes and bile ductal cells) of said warm-blooded vertebrate. The present tissue graft composition can be implanted, or fluidized and injected, into a vertebrate host to contact damaged or defective tissues and induce the repair or replacement of said tissues. The compositions of the present invention can also be applied as a component of a wound dressing (ointment or bandage) in fluidized or solid form for topical application to promote wound healing. Alternatively, the liver tissue derived extracellular matrix can be utilized as a cell growth substrate for growing eukaryotic cells in vitro.

DETAILED DESCRIPTION OF THE INVENTION

The tissue graft composition of the present invention comprises liver basement membrane prepared by separating same from the natively associated cellular components of liver tissue of a warm-blooded vertebrate. The preparative techniques described below provide an extracellular matrix composition consisting essentially of liver basement membrane substantially free of any cellular components. These compositions are referred to herein generically as liver basement membrane(s) (LBM). Other organ tissue sources of basement membrane for use in accordance with this invention include spleen, lymph nodes, salivary glands, prostate, pancreas and other secreting glands.

Basement membrane for use in the graft composition of this invention is typically prepared from liver tissue harvested from animals raised for meat production, including, for example, pigs, cattle and sheep or other warm-blooded vertebrates. Thus, there is an inexpensive commercial source of liver tissue for use in preparation of the tissue graft compositions in accordance with the present invention. In accordance with one embodiment, a composition comprising liver basement membranes is prepared from liver tissue of a warm-blooded vertebrate. This composition is useful as a non-immunogenic tissue graft capable of inducing endogenous tissue growth when implanted in warm-blooded vertebrates. In one embodiment, the composition comprises an extracellular matrix consisting essentially of liver basement membrane devoid of endogenous cells associated with the source vertebrate liver tissue used to prepared the composition.

The preparation of liver basement membrane from of liver tissue of a warm-blooded vertebrate in accordance with the present invention is carried out by removing the cellular components from liver tissue. Ideally the process is carried out to separate the cells from the basement membranes without damaging, or at least minimizing disruption or damage to, the basement membrane tissue. Removal of the cellular components from the liver extracellular matrix allows the preparation of a graft composition that is non-immunogenic, and thus does not induce a host immune response when the graft composition is implanted into a host. In general, the method for preparing a tissue graft composition from warm-blooded vertebrate liver tissue comprising the steps of treating the liver tissue with a cell dissociation solution for a period of time sufficient to release the cellular components of the liver tissue from the extracellular components without substantial disruption of the extracellular components, and separating the cellular components from said extracellular components. Typically the cell dissociation solution comprises a chaotropic agent or an enzyme or both.

The first step in preparing LBM in accordance to one embodiment of the present invention comprises slicing a segment of liver tissue into pieces (e.g., strips or sheets) to increase the surface area-to-volume ratio of the liver tissue. In one embodiment the liver tissue is sliced into a series of sheets each having a thickness of about 50 to about 500 microns, more preferably about 250 to about 300 microns. Freshly harvested liver tissue can be sliced using a standard meat slicer, or the tissue can be frozen and sliced with a cryomicrotone. The thin pieces of liver tissue are then treated with a solution that releases component liver cells from the associated extracellular basement membrane matrix.

In accordance with one embodiment the liver tissue is treated with a solution comprising an enzyme, for example, a protease, such as trypsin or pepsin. Because of the collagenous structure of the liver basement membrane and the desire to minimize degradation of the membrane structure during cell dissociation, collagen specific enzyme activity should be minimized in the enzyme solutions used in the cell-dissociation step. In addition, the liver tissue is typically also treated with a calcium chelating agent or chaotropic agent such as a mild detergent such as Triton 100. Thus, in one embodiment of this invention liver tissue is treated by suspending slices or strips of the tissue in a cell-dissociation solution containing enzyme(s) and chaotropic agent(s). However, the cell dissociation step can also be conducted using a calcium chelating agent or chaotropic agent in the absence of an enzymatic treatment of the tissue.

In one preferred embodiment the cell-dissociation step is carried out by suspending liver tissue slices in an agitated solution containing about 0.05 to about 2%, more typically about 0.1 to about 1% by weight protease, optionally containing a chaotropic agent or a calcium chelating agent in an amount effective to optimize release and separation of cells from the basement membrane without substantial degradation of the membrane matrix.

After contacting the liver tissue with the cell-dissociation solution for a time sufficient to release all cells from the matrix, the resulting liver basement membrane is rinsed one or more times with saline and optionally stored in a frozen hydrated state or a partially dehydrated state until used as described below. The cell-dissociation step may require several treatments with the cell-dissociation solution to release substantially all cells from the basement membrane. In one embodiment liver tissue is treated with a protease solution to remove the component cells, and the resulting extracellular matrix material (basement membrane) is further treated to remove or inhibit any residual enzyme activity. For example, the resulting basement membrane can be heated or treated with one or more protease inhibitors.

Liver basement membrane in accordance with this invention can be fluidized (converted to an injectable or powder form) in a manner similar to the preparation of fluidized intestinal submucosa, as described in U.S. Pat. No. 5,275,826 the disclosure of which is expressly incorporated herein by reference. Liver basement membrane (devoid of cells from the source liver tissue) is comminuted by tearing, cutting, grinding, shearing and the like. Grinding the liver basement membrane in a frozen or freeze-dried state is preferred although good results can be obtained as well by subjecting a suspension of liver basement membrane to treatment in a high speed (high shear) blender and dewatering, if necessary, by centrifuging and decanting excess water. Additionally, the comminuted fluidized tissue can be solubilized by enzymatic digestion with a protease, for example a collagenase and or other appropriate enzyme, such as glycanase, or other enzyme that disrupts the matrix structural components, for a period of time sufficient to solubilize said tissue and form a substantially homogeneous solution.

The present invention also contemplates the use of powder forms of liver basement membrane. In one embodiment a powder form of liver basement membrane is prepared by pulverizing liver basement membrane submucosa tissue under liquid nitrogen to produce particles ranging in size from 0.1 to 1 $mm^2$. The particulate composition is then lyophilized overnight and sterilized to form a solid substantially anhydrous particulate composite. Alternatively, a powder form of liver basement membrane can be formed from fluidized liver basement membranes by drying the suspensions or solutions of comminuted/liver basement membrane. The dehydrated forms have been rehydrated and used as cell culture substrates as described below without any apparent loss of their ability to support cell growth.

To determine the components of the isolated liver basement membranes of the present invention, the membranes have been extracted and the isolated fractions analyzed by Western blot analysis. LBM was extracted with guanidine hydrochloride or urea, as described in Example 4 and Western blot analysis, using antibodies directed against various specific growth factors, indicated the presence of basic growth fibroblast growth factor (bFGF), hepatocyte growth factor (HGF) and epidermal growth factor The present liver basement membrane compositions may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For instance, it is believed that strong gamma radiation may cause loss of strength in the graft material. Preferred sterilization techniques include exposing the graft to peracetic acid, low dose gamma irradiation and gas plasma sterilization; peracetic acid sterilization being the most preferred method. In particular, LBM has been disinfected and sterilized through the use of either peracetic acid or one megarad of gamma irradiation without adversely effecting the mechanical properties or biological properties of the tissue. The treatment with peracetic acid is conducted at a pH of about 2 to about 5 in an aqueous ethanolic solution (2–10% ethanol by volume) at a peracid concentration of about 0.03 to about 0.5% by volume. Typically, after the graft composition has been sterilized, the composition is wrapped in a porous plastic wrap and sterilized again using electron beam or gamma irradiation sterilization techniques.

In accordance with one embodiment, liver basement membrane is used as, or used to prepare, tissue graft compositions of the present invention. Such tissue graft compositions lend themselves to a wide variety of surgical applications relating to the repair or replacement of damaged tissues, including, for example the repair of connective tissues. Connective tissues for the purposes of the present invention includes bone, cartilage, muscle, tendons, ligaments, and fibrous tissue including the dermal layer of skin.

In accordance with this invention, the present tissue graft compositions are used advantageously to induce the formation of endogenous tissue at a desired site in a warm blooded vertebrate. Compositions comprising an extracellular matrix, consisting essentially of liver basement membrane, can be administered to a vertebrate host in an amount effective to induce endogenous tissue growth at a site in the host in need of same due to the presence of damaged or diseased tissue. The present liver tissue derived tissue graft compositions can be administered to the host in either solid form, by surgical implantation, or in fluidized form, by injection.

The liver basement membrane segments can be used in accordance with this invention as a tissue graft construct for use in the repair or replacement of connective tissues using the same procedures described for use of intestinal submucosa in U.S. Pat. Nos. 5,281,422 and 5,352,463, each expressly incorporated herein by reference.

The tissue graft compositions formed and used in accordance with this invention, upon implantation, undergo biological remodeling. They serve as a rapidly vascularized matrix for supporting the growth of new endogenous connective tissue. When used as a tissue graft material liver basement membrane is expected to be trophic for host tissues with which it is attached or otherwise associated in its implanted environment.

The liver basement membrane graft composition can be formed in a variety of shapes and configurations, for example, to serve as a ligament or tendon replacement or a patch for a broken or severed tendon or ligament. Preferably, the segment is shaped and formed to have a layered or even a multilayered configuration with at least the opposite end portions and/or opposite lateral portions being formed to have multiple layers of the graft material to provide reinforcement for attachment to physiological structures, including bone, tendon, ligament, cartilage and muscle. In a ligament replacement application, opposite ends are attached using standard surgical technique to first and second bones, respectively, the bones typically being articulated as in the case of a knee joint.

The end portions of the liver basement membrane graft composition can be formed, manipulated or shaped to be attached, for example, to a bone structure in a manner that will reduce the possibility of graft tearing at the point of attachment. Preferably the material can be folded or to provide multiple layers for gripping, for example, with spiked washers or staples.

Alternatively, the liver basement membrane graft material may be folded back on itself to join the end portions to provide a first connective portion to be attached, for example, to a first bone and a bend in the intermediate portion to provide a second connective portion to be attached to a second bone articulated with respect to the first bone. For example, one of the end portions may be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, ie, a tensioning and positioning function provided by a normal ligament.

The liver basement membranes of the present invention have been implanted in rabbits and in dogs to serve as Achilles tendon replacement graft constructs. Two rabbits and two dogs were each implanted with Achilles tendon replacement LBM graft constructs using a similar procedure as used for intestinal submucosal tissue as describe in U.S. Pat. No. 4,902,508. The experiments demonstrated that LBM graft constructs could support the regeneration of the Achilles tendon.

During preparation of the liver basement membrane, the tissue is cut or sliced into pieces/slices. After the cell-dissociation processing step the individual segments of liver basement membrane can be overlapped with one another and bonded together using standard techniques known to those skilled in the art, including the use of sutures, crosslinking agents, and adhesives or pastes. Alternatively, in one embodiment, the overlapped layers of submucosal tissue are fused to one another by applying pressure to the overlapped regions under dehydrating conditions. The term "dehydrating conditions" is defined to include any mechanical or environmental condition which promotes or induces the removal of water from the submucosal tissue. To promote dehydration of the compressed submucosal tissue, at least one of the two surfaces compressing the tissue is water permeable. Dehydration of the tissue can optionally be further enhanced by applying blotting material, heating the tissue or blowing air across the exterior of the compressing surfaces. Accordingly, multilayer liver basement membrane constructs can be prepared to provide tissue graft compositions of enhanced strength.

In addition, by overlapping a portion of one piece of liver basement membrane with a portion of at least one additional piece of liver basement membrane and bonding the overlapped layers to one another, large area sheets of liver basement membrane can be formed. In one embodiment, during formation of the large area sheets of tissue, pressure is applied to the overlapped portions under dehydrating conditions by compressing the overlapped tissue segments between two surfaces. The two surfaces can be formed from a variety of materials and in any shape depending on the desired form and specification of the targeted graft construct. Typically the two surfaces are formed as flat plates but they can also include other shapes such as screens, opposed cylinders or rollers and complementary nonplanar surfaces. Each of these surfaces can optionally be heated or perforated. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

The liver basement membrane can be compressed in accordance with one embodiment by placing the overlapped portions of the strips of cell-dissociated liver membrane on a first surface and placing a second surface on top of the exposed membrane surface. A force is then applied to bias the two surfaces towards one another, compressing the membrane composition between the two surfaces. The biasing force can be generated by any number of methods known to those skilled in the art including the passage of the apparatus through a pair of pinch rollers (the distance between the surface of the two rollers being less than the original distance between the two plates), the application of a weight on the top plate, and the use of a hydraulic press or the application of atmospheric pressure on the two surfaces.

In one preferred embodiment, a multi-layered liver basement membrane graft material is prepared without the use of adhesives or chemical pretreatments by compressing at least the overlapped portions of submucosal tissue under conditions that allow dehydration of the material concurrent with the compression of the tissue. To promote dehydration of the compressed material, at least one of the two surfaces compressing the tissue is water permeable. Dehydration can optionally be further enhanced by applying blotting material, heating the material or blowing air across the exterior of the two compressing surfaces. The compressed multi-layered liver basement membrane material can be removed from the two surfaces as a unitary compliant large area graft construct. The construct can be further manipulated (i.e., cut, folded, sutured, etc.) to suit various medical applications where the liver basement membrane material is required.

A vacuum can optionally be applied to liver basement membrane during the compression procedure. The applied vacuum enhances the dehydration of the tissue and may assist the compression of the tissue. Alternatively the application of a vacuum may provide the sole compressing force for compressing the overlapped portions of the multiple layers of liver basement membranes. For example, in one embodiment the overlapped liver basement membrane is laid out between two surfaces, preferably one of which is water permeable. The apparatus is covered with blotting material, to soak up water, and a breather blanket to allow air flow. The apparatus is then placed in a vacuum chamber and a vacuum is applied, generally ranging from 35.6–177.8 cm of Hg (0.49–2.46 Kg/cm$^2$) and more preferably the vacuum applied is approximately 129.5 cm of Hg (1.76 Kg/cm$^2$). Optionally a heating blanket can be placed on top of the chamber to heat the liver basement membrane during compression. Chambers suitable for use in this embodiment are known to those skilled in the art and include any device that is equipped with a vacuum port. The resulting drop in atmospheric pressure coacts with the two surfaces to compress the tissue and simultaneously dehydrate the compressed tissue.

In an alternative embodiment of the present invention, liver basement membrane can be utilized in a method and composition for supporting the proliferation and induction of tissue differentiation of eukaryotic cells cultured in vitro. Generally the method comprises the step of contacting eukaryotic cells, in vitro, with a liver basement membrane composition under conditions conducive to eukaryotic cell growth. The term "contacting" as used herein with reference to cell culture is intended to include both direct and indirect contact, for example in fluid communication, of the liver basement membrane composition and the cultured cells. The term "conditions conducive to eukaryotic cell growth" as used herein refers to the environmental conditions, such as sterile technique, temperature and nutrient supply, that are considered optimal for eukaryotic cell growth under currently available cell culture procedures. Although optimum cell culture conditions used for culturing eukaryotic cells depend somewhat on the particular cell type, cell growth conditions are generally well known in the art. However a number of differentiated cell types are still considered difficult to culture (i.e., islets of Langerhans, hepatocytes, chondrocytes, osteoblasts, etc.).

Applicants have discovered that compositions comprising liver basement membrane prepared in accordance with this invention can be used for supporting growth or proliferation of eukaryotic cells in vitro. In accordance with one embodiment a liver tissue derived composition for supporting the growth of a cell population is prepared from liver tissue of a warm-blooded vertebrate. The composition comprises isolated liver basement membrane devoid of source liver tissue endogenous cells and added nutrients to support the growth of said cell population in vitro. In addition fluidized forms of liver basement membrane can be used to coat culture-ware with a matrix comprising liver basement membrane devoid of source liver tissue endogenous cells. Thus, liver basement membrane can be used as a cell growth substrate in a variety of forms, including a sheet-like configuration, as a gel matrix, as an additive for art-recognized cell/tissue culture media, or as coating for culture-ware to provide a more physiologically relevant substrate that supports and enhances the proliferation of cells.

The liver basement membrane, due to its honeycomb-like structure (that which remains after cell-dissociation) provides a high surface area for cell adhesion and also induces cell differentiation. Scanning electron images indicate that the isolated liver basement membrane is very porous. When fetal rat cells are cultured on liver basement membranes that are retained in their nature three dimensional shape, scanning electron images reveal that the fetal rat cells form confluent sheets on the liver cell substrate and also invade into the LBM matrix. The membrane material is preferably sterilized prior to use in cell culture applications, however nonsterile material can be used if antibiotics are included in the cell culture system.

In one preferred embodiment cells are seeded directly onto sheets of liver basement membrane under conditions conducive to eukaryotic cell proliferation. The highly porous nature of the liver basement membrane allow diffusion of cell nutrients throughout the membrane matrix. Thus, cells can be cultured on or within the liver basement membrane matrix.

In another embodiment of the present invention, cell growth substrates are formed from fluidized forms of liver basement membrane. The fluidized tissue can be gelled to form a solid or semi-solid matrix. The viscosity of fluidized tissue for use in accordance with this invention can be manipulated by controlling the concentration of the tissue component and the degree of hydration. The viscosity can be adjusted to a range of about 2 to about 300,000 cps at 25° C. Higher viscosity formulations, for example, gels, can be prepared from the digest solutions by adjusting the pH of such solutions to about 6.0 to about 7.4. Eukaryotic or prokaryotic cells can then be seeded directly on the surface of the matrix and cultured under conditions conducive to eukaryotic cell proliferation.

The cell growth substrates of the present invention can be combined with nutrients; including minerals, amino acids, sugars, peptides, proteins, or glycoproteins that facilitate cellular proliferation, such as laminin and fibronectin and growth factors such as epidermal growth factor, platelet-derived growth factor, transforming growth factor beta, or fibroblast growth factor. In one embodiment fluidized or powder forms of liver basement membrane can be used to supplement standard eukaryotic culture media to enhance the standard media's capacity for sustaining and inducing the proliferation of cells cultured in vitro.

In accordance with the present invention there is provided a cell culture composition for supporting growth in vitro of an eukaryotic cell population in combination with liver basement membrane of a warm-blooded vertebrate. The composition comprises liver basement membrane substantially free of the original associated endogenous cells. The composition can further comprise nutrients, and growth factors required for optimal growth of the cultured cells. The liver basement membrane cell culture substrate can be used with commercially available cell culture liquid media (both serum based and serum free). Proliferating cells can either be in direct contact with the liver basement membrane or they can simply be in fluid communication with the liver basement membrane.

It is anticipated that cell growth compositions utilizing the liver basement membrane composition of the present invention can be used to stimulate proliferation of undifferentiated stems cells as well as differentiated cells such as islets of Langerhans, hepatocytes and chondrocytes. Furthermore, the described cell growth composition is believed to support the growth of differentiated cells while maintaining the differentiated state of such cells. Several primary cell lines have been grown on LBM derived cell culture substrates in vitro, including primary cell lines derived from the cruciate ligament. Primary cell lines derived from the cruciate ligament show an approximate doubling of the growth rate compared to when these cells are grown on plastic.

It is anticipated that liver basement membrane is capable of inducing host tissue proliferation, remodeling and regeneration of appropriate tissue structures upon implantation in a number of microenvironments in vivo (e.g., tendon, ligament; bone, articular cartilage, artery, and vein). In one embodiment of the present invention the tissue replacement capabilities of graft compositions comprising liver basement membrane of warm-blooded vertebrates are further enhanced or expanded by seeding the tissue with various cell types, prior to implantation. For example, a liver basement membrane derived cell culture substrate may be seeded with endothelial cells or keratinocytes for use as a vascular graft or skin replacement, respectively. Alternatively, the liver basement membrane can be seeded with mesenchymal cells (stem cells) initially for expansion of the cell population and thereafter for implantation into a host. Liver basement membrane can also serve as a delivery vehicle, either in fluidize form or in its native solid form, for introducing various cell populations, including genetically modified cells, to a specific location in a host. Optionally, after the liver basement membrane have been seeded with eukaryotic cells, the graft composition can be subjected to conditions conducive to the proliferation of eukaryotic cells to further expand the population of the seeded cells prior to implantation of the graft into the host.

In another embodiment, compositions comprising liver basement membrane and a proliferating cell population can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (Science Vol. 210 pp. 908–910). Indeed, the present liver basement membrane composition itself could be used advantageously to encapsulate a proliferating cell population in accordance with this invention for implantation as an artificial organ.

EXAMPLE 1
Preparation of Liver Basement Membrane

| 2 mM EDTA Chaotropic Solution Used In The Experiment | |
|---|---|
| 140 mM | NaCl |
| 5 mM | KCl |
| 0.8 mM | $MgSO_4$ |
| 0.4 mM | $KH_2PO_4$ |
| 2 mM | EDTA |
| 25 mM | $NaHCO_3$ |

Procedure

Preparation of Liver Slices

Liver frozen in −70° C. was sliced with a cryomicrotone to a thickness of about 50 μM. The slices of liver tissue were then subjected to enzymatic treatment (trypsin) with a chaotropic solution (samples 1 and 2), with enzyme alone (samples 3 and 4), or with a chaotropic solution alone (sample 5), as indicated below.

| Sample # | Treatment |
|---|---|
| 1) | 0.05% Trypsin in 2 mM EDTA solution |
| 2) | 0.1% Trypsin in 2 mM EDTA solution |
| 3) | 0.05% Trypsin in 2 mM PBS |
| 4) | 0.1% Trypsin in 2 mM PBS |
| 5) | 2 mM EDTA solution |

Liver slices were placed in five 50 ml tubes, each of which contained 25 mL of a different buffered enzyme treatment solution. The liver tissue was incubated at 37° C. in water bath with gentle shaking for 1 hour. The liver slices were washed twice with PBS with agitation/shaking for 1 hour at room temperature. The above enzymatic treatment steps were repeated three times.

The wash buffers were collected and spin them down in 2000 rpm for 10 min. The pellet was suspended and an equal amount of trypan blue was added to identify any remaining cells. The material was checked for presence of cells under microscope.

EXAMPLE 2
Mechanical Properties of Isolated Liver Basement Membrane

Porosity of a graft material is typically measured in terms of ml of water passed per $cm^2 min^{-1}$ at a pressure of 120 mm Hg. The average "porosity index" established for two separate specimens of LBM was 1162. The suture retention strength of LBM is approximately 68 grams. The material appears to be anisotropic, with the suture strength being approximately the same in all directions.

EXAMPLE 3
Growth and Differentiation of Various Cell Lines on Liver Basement Membrane In the present study, the growth and differentiation of three different cell lines on liver basement membrane (LBM) was investigated. These tested cell lines included Swiss 3T3, a fibroblast cell line, ROS. 17/2.8, an osteosarcoma cell line and PC12, a neuronal cell line. All cells were seeded on a collagen coated plate. The seeding densities for Swiss 3T3 and ROS cells was $20 \times 10^4$ cells/ml, whereas the PC12 was seeded at $5 \times 10^4$ cells/ml. In order to compare the growth and differentiation of these cells lines on LBM and small intestinal submucosa (SIS), the same cells with same densities were also seeded on SIS. In addition, a positive control for PC12 cells was achieved by adding nerve growth factor (NGF) 50 ng/ml to the cells. All experiments were carried out in duplicate. After five days one sample from each cell line seeded on SIS and LBM was prepared for histology.

Preliminary observations indicate growth of all three cell lines and differentiation of ROS and PC12 cell lines on both substrates. A light microscopic observation of PC12 cells indicated a greater degree of differentiation on LBM compared to the cells grown on SIS. In addition, ROS and 3T3 cells appeared to grow/differentiate as well as they do on SIS. Due to the transparent nature of LBM, it was difficult to quantify the growth and differentiation of the cells, but the histological examination will allow a more detailed assessment.

EXAMPLE 4
Preparation of Extracts of LBM

Extraction buffers used for these studies included 4 M guanidine and 2 M urea each prepared in 50 mM Tris-HCl, pH 7.4. The powder form of LBM was suspended in the relevant extraction buffer (25% w/v) containing phenylmethyl sulphonyl fluoride, N-ethylmaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately or lyophilized for long term storage.

Western blot analysis with antibodies specific for bFGF HGF and EGF detected a corresponding reactive band for each of the antibodies, confirming the presence of these growth factors in LBM.

What is claimed is:

1. A method for inducing the formation of endogenous tissue at a site in need of endogenous tissue growth in a warm-blooded vertebrate, said method comprising implanting a graft composition comprising an extracellular matrix consisting essentially of basement membrane of liver tissue of a warm-blooded vertebrate in an amount effective to induce endogenous tissue growth at the site the graft composition is administered, said liver basement membrane being devoid of endogenous cells associated with said liver tissue.

2. The method of claim 1 wherein the basement membrane is fluidized and the graft composition is administered by injection into the warm-blooded vertebrate.

3. The method of claim 1 wherein the graft composition is administered by surgically implanting the composition into the warm-blooded vertebrate.

4. The method of claim 1 wherein the endogenous cells are dissociated with a cell dissociation solution.

5. The method of claim 4 wherein the cell dissociation solution comprises a chaotropic agent.

6. The method of claim 4 wherein the cell dissociation solution comprises a protease.

7. The method of claim 4 wherein the cell dissociation solution comprises EDTA and trypsin.

8. The method of claim 4 wherein the liver tissue is sliced into sheets or strips of liver tissue before the liver tissue is treated with the dissociation solution.

9. The method of claim 8 wherein the liver tissue is sliced into sheets or strips having a thickness of up to about 500 $\mu$.

10. The method of claim 1 further comprising the step of comminuting the extracellular matrix material to form a fluidized graft composition.

11. The method of claim 10 further comprising the step of enzymatically digesting the extracellular matrix material to form a fluidized graft composition.

12. The method of claim 1 further comprising the step of enzymatically digesting the extracellular matrix material to form a fluidized graft composition.

13. The method of claim 10 further comprising the step of drying the fluidized graft composition to the form of a dry powder.

14. The method of claim 11 further comprising the step of drying the fluidized graft composition to the form of a dry powder.

* * * * *